United States Patent [19]

Kussmaul et al.

[11] Patent Number: 5,489,647
[45] Date of Patent: Feb. 6, 1996

[54] HYDROPHILIC, SWELLABLE GRAFT POLYMERS

[75] Inventors: Ulrich Kussmaul, Karben; Manfred Mayer, Niedernhausen; Uwe Stüven, Bad Soden; Ulrich Riegel; Friedrich Engelhardt, both of Frankfurt am Main, all of Germany

[73] Assignee: Cassella Aktiengesellschaft, Germany

[21] Appl. No.: 977,002

[22] Filed: Nov. 16, 1992

[30] Foreign Application Priority Data

Nov. 30, 1991 [DE] Germany .......................... 41 39 613.8

[51] Int. Cl.⁶ .......................... C08F 251/00; C08F 283/06
[52] U.S. Cl. .......................... 525/54.3; 527/300; 527/312; 527/313; 527/314
[58] Field of Search .................................. 527/300, 312, 527/313, 314; 525/54.24, 54.3

[56] References Cited

U.S. PATENT DOCUMENTS

| | | | |
|---|---|---|---|
| Re. 32,957 | 6/1989 | Elias et al. . | |
| 4,076,663 | 2/1978 | Masuda et al. | 527/312 |
| 4,734,478 | 3/1988 | Tsubakimoto et al. | 527/300 |
| 4,755,562 | 7/1988 | Alexander et al. | 525/329.3 |
| 4,820,773 | 4/1989 | Alexander et al. | 525/285 |
| 4,931,497 | 6/1990 | Engelhardt et al. . | |
| 4,954,562 | 9/1990 | Anderson | 524/779 |
| 5,026,800 | 6/1991 | Kimura et al. | 526/200 |
| 5,053,460 | 10/1991 | Mallo et al. . | |
| 5,098,951 | 3/1992 | Mallo et al. . | |
| 5,154,713 | 10/1992 | Lind | 521/92 |
| 5,180,800 | 1/1993 | Heidel et al. | 527/300 |

FOREIGN PATENT DOCUMENTS 283090  10/1988  European Pat. Off. .

*Primary Examiner*—Jeffrey Mullis
*Attorney, Agent, or Firm*—Connolly & Hutz

[57] ABSTRACT

The present invention relates to hydrophilic, swellable graft polymers which comprise, in a random distribution, from 0.5 to 50% by weight of radicals of the general formula I

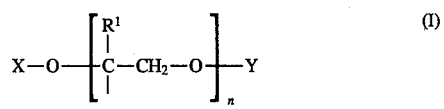

and radicals of the general formula II

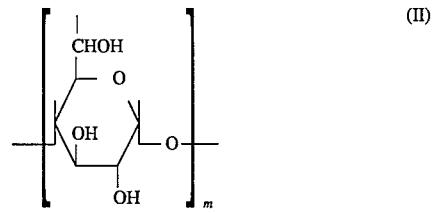

from 49 to 99% by weight of radicals of the general formula III

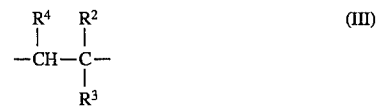

containing an acid group, and from 0.1 to 2% by weight of radicals of a crosslinking agent which are derived from monomers containing at least two olefinically unsaturated double bonds, where the radicals $R^1$ to $R^4$, X and Y and n and m are where X and Y, independently of one another are $COCH_3$, $CH_2COOR^2$, $COCH_2CH_2COOH$

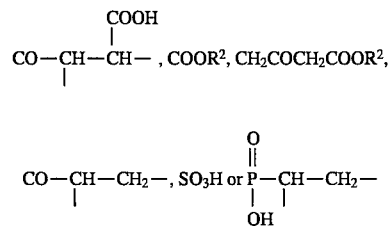

n and m, independently of one another, are 2 to 300, $R^1$ is hydrogen or methyl, $R^2$, independently of one another, are hydrogen, methyl or ethyl, $R^3$ is the carboxyl group, the sulphonyl group, the phosphonyl group, which is optionally esterified by means of alkanol having 1 to 4 carbon atoms, or a group of the formula

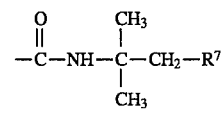

to the preparation thereof, and to the use thereof as absorbents for water and aqueous solutions.

13 Claims, No Drawings

HYDROPHILIC, SWELLABLE GRAFT POLYMERS

The present invention relates to hydrophilic, swellable graft polymers, to the preparation thereof, and to the use thereof as absorbents for water and aqueous solutions, for example in hygiene articles, for improving the soil or as filtration aids.

Swellable polymers which absorb aqueous solutions are used for the production of tampons, nappies, sanitary towels and other hygiene articles and as water-retaining agents in horticulture.

The known absorption resins of this type include crosslinked carboxymethylcellulose, partially crosslinked polyalkylene oxide, hydrolysates of starch-acrylonitrile graft copolymers, partially crosslinked polyacrylic acid salts and graft polymers as described in EP-A 400 238.

These known polymers all have disadvantages, in particular in the absorption of aqueous electrolyte solution, blood and urine.

For a high absorption capacity, the current state of the art achieves inadequate gel strengths of the swollen polymer particles. Tacky materials form which impair the absorbency of the products produced therewith.

It is known that the gel strength and the rate of liquid absorption can be increased by increasing the crosslinking density, but this simultaneously reduces the absorption capacity. This procedure is undesired inasmuch as the absorption capacity is the most important property of the polymer.

In addition, the known polymers tend to stick to hot steel surfaces, for example to the surfaces of roller driers, which makes drying much more difficult. In particular, such polymers cannot be dried sufficiently quickly.

It is an object of the present invention to provide modified polymers which absorb aqueous solutions, have a high absorption rate, form hydrogel particles of high gel strength which are non-tacky in the swollen state, and do not tend to stick to hot steel surfaces.

The present invention relates to hydrophilic, swellable graft polymers which comprise, in a random distribution, from 0.5 to 50% by weight of radicals of the general formula I

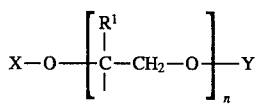

and radicals of the general formula II

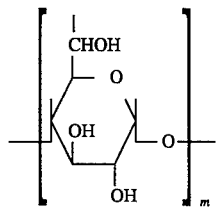

from 49 to 99% by weight of radicals of the general formula III

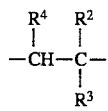

containing an acid group, and from 0.1 to 2% by weight of radicals of a crosslinking agent which are derived from monomers containing at least two olefinically unsaturated double bonds, where X is $(C_1-C_{22})$-alkyl, aryl, aralkyl or Y, Y is $$COCH_3, CH_2COOR^2, COCH_2CH_2COOH,$$

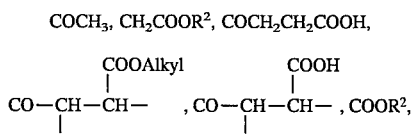

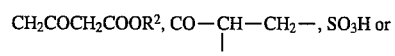

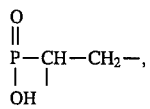

n and m, independently of one another, are 2 to 300, $R^1$ is hydrogen or methyl, the radicals $R^2$, independently of one another, are hydrogen, methyl or ethyl, $R^3$ is the carboxyl group, the sulphonyl group, the phosphonyl group, which is optionally esterified by means of alkanol having 1 to 4 carbon atoms, or a group of the formula

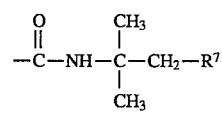

in which $R^7$ is the sulphonyl group or the phosphonyl group, and $R^4$ is hydrogen, methyl, ethyl or the carboxyl group.

Preferred products according to the invention comprise from 0.5 to 20% by weight of radicals of the general formulae I and II, from 79 to 99% by weight of radicals of the general formula III and from 0.1 to 1.8% by weight of crosslinking structures which are derived from monomers containing at least two olefinically unsaturated double bonds.

Particularly preferred products according to the invention comprise from 1 to 15.5% by weight of radicals of the general formulae I and II, from 83 to 98.5% by weight of radicals of the general formula III and from 0.3 to 1.5% by weight of crosslinking structures which are derived from monomers containing at least two olefinically unsaturated double bonds.

The weight ratio between the radicals of the general formulae I and II is preferably 1:99 to 99:1. The weight ratio between the radicals of the general formulae I and II is particularly preferably 50:50 if the proportion of the sum of the radicals of the general formulae I and II in the entire polymer is less than 10% by weight and from 10:90 to 25:75 if the proportion of the sum of the radicals of the general formulae I and II in the entire polymer is from 10 to 50% by weight.

In the graft copolymers according to the invention, the radicals of the general formula I may all have precisely the same structure, but they may also differ from one another with respect to the radical $R^1$ and/or the number n. Thus, hydrogen and methyl may alternate in a random manner with respect to $R^1$, but it is also possible for relatively large polymer segments in which $R^1$ is either only hydrogen or only methyl to follow one another.

Aryl representing X preferably has 3 to 8 carbon atoms and is particularly preferably phenyl, tert.-butylphenyl or nonylphenyl. Aralkyl representing X preferably has 3 to 8 carbon atoms in the aryl radical and 1 to 22 carbon atoms in the alkyl radical.

The alkyl group of the radical representing Y

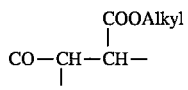

has 1 to 22 carbon atoms.

Y is preferably $COCH_3$, $CH_2COOR^2$, $COCH_2CH_2COOH$, $COOR^2$ $CH_2COCH_2COOR^2$ and

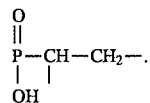

The radicals of the general formula II are derived from starch or starch-degradation products.

In the radicals of the general formula III, $R^2$ is preferably hydrogen or methyl. $R^3$ is preferably the carboxyl group, the sulphonyl group or the phosphonyl group. The carboxyl group is particularly preferred. $R^4$ is preferably hydrogen.

Said crosslinking structures may be derived from all suitable monomers containing at least two olefinically unsaturated double bonds.

Examples of suitable monomers are compounds containing at least two alkenyl groups, for example vinyl or allyl, or at least two alkenoyl groups, for example acrylate or methacrylate.

The crosslinking structures are preferably derived from monomers containing 2, 3 or 4 ethylenically unsaturated double bonds.

The crosslinking structures are particularly preferably derived from trimethylolpropane triacrylate, tetraallyloxyethane or methylenebisacrylamide.

Further crosslinking structures may be obtained by addition of polyfunctional epoxides, such as, for example, ethylene glycol diglycidyl ether or a cycloaliphatic diepoxide.

Very particularly preferred graft polymers according to the invention are those in which more than one of the above-mentioned preferred or particularly preferred features are present.

The graft polymers according to the invention can be prepared by known polymerisation processes. Preference is given to polymerisation in aqueous solution by the gel polymerisation process. In this, 15–50% strength aqueous solutions of the comonomers are polymerised by means of known suitable catalyst systems without mechanical mixing, utilising the Trommsdorff-Norrish effect (Bios Final Rep. 363.22; Makromol. Chem. 1, 169 (1947)).

The polymerisation reaction can be carried out in the temperature range between 0° C. and 130° C., preferably between 10° C. and 100° C., either at atmospheric pressure or under increased pressure. As usual, the polymerisation can also be carried out in a protective-gas atmosphere, preferably under nitrogen.

The polymerisation can be initiated using high-energy electromagnetic rays or conventional chemical polymerisation initiators, for example organic peroxides, such as benzoyl peroxide, tert.-butyl-hydroperoxide, methyl ethyl ketone peroxide, cumene hydroperoxide, azo compounds, such as azobisisobutyronitrile, and inorganic peroxy compounds, such as $(NH_4)_2S_2O_8$ or $K_2S_2O_8$ or $H_2O_2$, if necessary in combination with reducing agents, such as sodium hydrogen sulphite, and iron(II) sulphate, or redox systems containing, as reducing component, an aliphatic or aromatic sulphinic acid, such as benzenesulphinic acid or toluenesulphinic acid, or derivatives of these acids, such as, for example, Mannich adducts of sulphinic acid, aldehydes and amino compounds, as described in German Patent 13 01 566. In general, from 0.03 to 2 g of the polymerisation initiator are employed per 100 g of total monomers.

The quality properties of the polymers can be further improved by subsequently heating the polymer gels for several hours in the temperature range from 50°–130° C., preferably 70°– 100° C.

The novel copolymers prepared by this method, which are in the form of aqueous gels, can be obtained and used in solid form by known drying processes after mechanical comminution using suitable equipment.

Graft polymers according to the invention are thus expediently obtained if from 0.5 to 50% by weight, preferably from 0.5 to 20% by weight, in particular from 1 to 15.5% by weight, of a mixture of a polyalkylene oxide compound of the general formula Ia

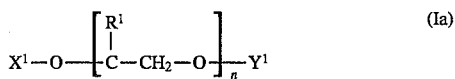

or, if desired, an alkali metal salt, ammonium salt or amine salt thereof, and a compound of the general formula IIa

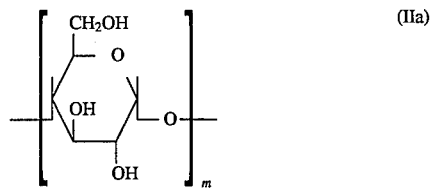

from 49 to 99% by weight, preferably from 79 to 99% by weight, in particular from 83 to 98.5% by weight, of an unsaturated acid of the general formula IIIa

or an alkali metal salt, ammonium salt or amine salt thereof, and from 0.1 to 2% by weight, preferably from 0.1 to 1.8% by weight, in particular from 0.3 to 1.5% by weight, of a monomer containing at least two olefinically unsaturated double bonds, where $X^1$ is $(C_1-C_{22})$-alkyl, aryl, aralkyl or Y, $Y^1$ is $COCH_3$, $CH_2COOR^2$, $COCH_2CH_2COOH$, CO—CH=CH—COOalkyl, CO—CH=CH—COOH, $COOR^2$, $CH_2COCH_2COOR^2$, CO—CH=CH$_2$, $SO_3H$ or

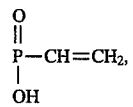

and the radicals $R^1$ to $R^4$ and the numbers n and m are as defined above, are reacted under the conditions of gel polymerisation.

The polyalkylene oxide compounds of the general formula Ia can be obtained by known conversion reactions of compounds containing reactive groups, such as anhydrides, acid chlorides, halocarboxylic acids or esters thereof, or halosulphonic acids and polyalkylene oxides.

Preferred polyalkylene oxides are polypropylene oxides and polyethylene oxides, copolymers or block copolymers made from ethylene oxide and propylene oxide, oxyethylates, oxypropylates or oxyethyloxypropylates of aliphatic $C_1$ to $C_{22}$-alkylalcohols, phenol, tert.-butylphenol or nonylphenol.

Preferred reagents for terminating the polymer chain are chloroacetoacetic acid and esters thereof, chloroformic acid and esters thereof, vinylphosphonic acid monochloride and dichloride, succinic anhydride, acetic anhydride and monochloroacetic acid.

Preferred compounds of the general formula IIa are starches. All native and/or modified starches of various origins can be used here. Starches obtained from roots and tubers of various plants, such as, for example, potatoes, arrowroot or cassava, can be employed, as can those obtained from cereal seeds, such as, for example, maize, wheat, rice and barley, those obtained from fruit, such as, for example, chestnuts, peas and beans, or those obtained from pith, such as, for example, that of the sago palm.

Particularly preferred compounds of the general formula IIa are maize starch and potato starch.

The monomers of the formula IIIa are known compounds, such as, for example, acrylic acid, methacrylic acid, vinylsulphonic.acid, maleic acid, fumaric acid, crotonic acid, 2-acrylamido- 2-methylpropanesulphonic acid, 2-acrylamido-2-methylpropanephosphonic acid and vinylphosphonic acid, and monoesters thereof.

The polyolefinic monomers employed as crosslinking agents are conventional products. Examples are bisacrylamidoacetic acid, trimethylolpropane triacrylate, tetraallyloxyethane and methylenebisacrylamide.

Particularly preferred polymers according to the invention are those which are mechanically comminuted after the above-described preparation and are modified by application of carboxyl-reactive compounds to the surface of the polymer particles.

Examples of suitable carboxyl-reactive compounds are polyhydric alcohols, polyalcohols, polyepoxides, (poly)glycidyl ethers, diglycidyl phosphonates, polyamines, polyoxazolines, polyaziridines, alkoxysilylamines, alkoxysilane epoxides, polyamidoamines, polyquarternary substances and polyvalent metal cations.

Preferred carboxyl-reactive compounds are glycidyl ethers of polyhydric alcohols, such as, for example, monoethylene glycol diglycidyl ether, polyethylene glycol diglycidyl ether, in particular nonaethylene glycol diglycidyl ether, monopropylene glycol diglycidyl ether and polypropylene glycol diglycidyl ether; glycidyl phosphonates of the general formula IV

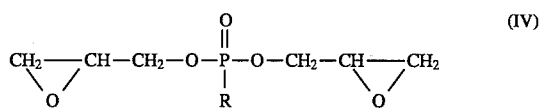
(IV)

in which R is alkyl, alkenyl or aryl, each of which is optionally substituted;

polymeric compounds, such as, for example, polyamines or polyamidoamines, which are prepared in a known manner by condensation of aliphatic dicarboxylic acids with diamines or polyamines, such as, for example, diethylenetriamine, and may also be quaternised;

alkoxysilyl compounds, such as, for example, aminoalkylalkoxysilanes, in particular 3-aminopropyltriethoxysilane, trimethoxysilylpropyldiethylenetriamine, N-aminoethylaminopropyltrimethoxysilane and aminoethylaminomethylphenethyltrimethoxysilane, and glycidylalkoxysilanes, in particular 3-glycidyloxypropyltrimethoxysilane; and highly reactive silicic acid sols.

In the general formula IV, R is preferably $(C_1-C_{18})$-alkyl; $(C_3-C_8)$-cycloalkyl; a group of the general formula V

(V)

in which $R^5$ and $R^6$, independently of one another, are hydrogen or $(C_1-C_4)$-alkyl; or a group of the general formula VI

(VI)

in which $R^7$ is hydrogen, halogen or $(C_1-C_4)$-alkyl.

Said carboxyl-reactive compounds may also be used in mixtures with one another or stepwise one after the other.

The carboxyl-containing compounds are preferably applied to the polymer particles by mixing the components in a mixer.

Examples of suitable mixers are Patterson-Kelly mixers, DRAIS turbulence mixers, Lödige mixers, screw mixers, plate mixers and fluidised-bed mixers.

The process is preferably carried out in the temperature range between 0° and 200° C., preferably between 10° and 80° C. It is preferred to prewarm the polymer particles to a temperature of from 40° to 100° C. before carrying out the process. In a preferred embodiment, the components are mixed in a conventional, heatable mixer at a temperature between 20° and 60° C. and then heated to a temperature between 80° and 200° C., preferably 80° to 150° C., in order to accelerate the reaction in the region close to the surface. In a further preferred embodiment, this heat-treatment step is carried out in a subsequent dryer for a period of from 10 minutes to 6 hours, it being possible for elimination products, which can be produced during the reaction, and any solvent components which had previously been added to be removed.

The carboxyl-reactive compounds can be employed as they are or in the form of solutions.

Preferred solvents are water, alcohols, esters, ketones, ethers and hydrocarbons, and mixtures of these components, having boiling points of up to 200° C., preferably up to 150° C.

The carboxyl-reactive compound are preferably employed in amounts of from 0.01 to 10% by weight, particularly preferably 0.05. to 3% by weight, based on the polymer particles to be modified.

The graft polymers according to the invention are highly suitable as absorbents for water and aqueous solutions, and they can thus advantageously be employed as water-retaining agents in horticulture, as filtration aids and particularly as the absorptive component in hygiene articles, such as nappies, tampons or sanitary towels.

It is particularly advantageous that the graft polymers according to the invention do not tend to stick to hot steel surfaces, such as, for example, the surfaces of roller dryers, and a high drying rate is thus ensured.

In the examples below, the following compounds of the general formula Ia are used:

A:

20.0 g of succinic anhydride are introduced with stirring at room temperature into 312 g of a block copolymer comprising 1.03 mol of propylene oxide and 0.91 mol of ethylene oxide and having an OH number of 36, and this mixture is heated to 80° C. with stirring. During this operation, the succinic anhydride dissolves in a slightly exothermic reaction; a clear colourless solution is formed.

B:

1010 g (0.495 mol) of polypropylene glycol 2020 are dissolved in 500 ml of toluene in a 4-neck flask with azeotrope attachment and nitrogen inlet, and the water is removed from the solution, i.e. the mixture is subjected to azeotropic distillation for 3 hours, 43 g of water being separated off. 12.5 g (1.1 mol) of acetic anhydride are added dropwise at 105°–110° C. over the course of 30 minutes, and the mixture is stirred for a further 2 hours at 105°– 110° C. Toluene, acetic acid and excess acetic anhydride are removed by distillation under a water-pump vacuum. 1020 g of a colourless oil remain as the residue.

C:

4621 g (1.0 mol) of a polyglycol ether based on nonylphenol containing 100 ethylene oxide units are melted. 102 g (1.0 mol) of acetic anhydride are added dropwise at 90°–100° C., the mixture is stirred for 30 minutes and the acetic acid formed is then removed by distillation under a water-pump vacuum. A colourless solution is formed which solidifies at room temperature to give a solid wax.

D:

345 g of a block polymer comprising 1.6 mol of propylene oxide and 0.2 mol of ethylene oxide and having an OH number of 65 are dissolved in 350 ml of ethyl acetate in a reaction flask, 40.5 g of triethylamine are added, and 37.8 g of monochloroacetic acid are added slowly. The mixture is stirred for a further 1 hour, the triethylamine hydrochloride is filtered off with suction, and the solvent is removed by distillation under a water-pump vacuum. 368 g of a colourless oil remain as the residue.

E:

Reaction analogous to A with a copolymer comprising 0.35 mol of propylene oxide and 1.82 mol of ethylene oxide and having an OH number of 17.

F:

Reaction analogous to A with a copolymer comprising 1.6 mol of propylene oxide and 0.2 mol of ethylene oxide and having an OH number of 65.

G:

Reaction analogous to D with nonylphenol oxyethylate containing 30 ethylene units and ethyl chloroacetoacetate.

H:

Reaction analogous to D with nonylphenol oxyethylate containing 30 ethylene units and chloroformic acid.

I:

Reaction analogous to D with a copolymer comprising 1.03 mol of propylene oxide and 0.91 mol of ethylene oxide and having an OH number of 36, and vinylphosphonic acid monochloride.

K:

Reaction analogous to D with polypropylene glycol 2020 and monochloroacetic acid.

L:

Reaction analogous to C with tert.-butylphenol oxyethylate containing 80 ethylene oxide units and acetic anhydride.

M:

Reaction analogous to D with phenol oxyethylate containing 15 propylene oxide units and vinylphosphonic acid dichloride.

N:

Reaction analogous to B with polyethylene glycol 300 (1.0 mol) and maleic anhydride (1.98 mol).

EXAMPLE 1

4,430 g of demineralised water are introduced into a polyethylene bucket with a capacity of 10 l which is well insulated by foamed plastic material, 1,493 g of sodium bicarbonate are dispersed therein, and 1,910 g of acrylic acid are slowly metered in at such a rate that the reaction solution is prevented from foaming over, the solution being cooled to a temperature of about 12°–10° C. 40 g of the product from A (see above), 490 g of a starch solution, which has been boiled and likewise cooled to 10° C., of 45 g of commercially available maize starch and 445 g of demineralised water, 20 g of trimethylolpropane triacrylate, dissolved in 20 g of a polyglycol ether based on a synthetic $C_{12}$-$C_{15}$-oxo alcohol containing 13 ethylene oxide units, and 10 g of a sodium diisooctylsulphosuccinate (REWOPOL V 2133 from REWO, Steinau) are then added. At a temperature of 10°–12° C., the initiators, a redox system comprising 2.2 g of 2,2'-azobisamidinopropane dihydrochloride, dissolved in 20 g of water, 4.4 g of potassium peroxydisulphate, dissolved in 170 g of water, and 6 g of sodium pyrosulphite, dissolved in 120 g of water, are added successively, and the mixture is stirred vigorously. The reaction solution is then left to stand without stirring, a solid gel forming due to commencing polymerisation, during the course of which the temperature increases to about 85° C. This gel is subsequently comminuted mechanically, dried at temperatures above 80° C. and ground.

The above described product was incorporated in a conventional manner into a baby's nappy, where it was distinguished by particularly good liquid retention.

EXAMPLE 2

4,419 g of ice and 1,894 g of acrylic acid are introduced into a 10 liter plastic bucket, and 1,573 g of 50% strength NaOH are slowly metered in, and subsequently 100 g of the product from A) (see above), 275 g of a starch solution, which has been boiled and cooled down to 20° C., of 25 g of commercially available potato starch and 250 g of softened water, and 6 g of methylenebisacrylamide, dispersed in 100 g of water, are added. The reaction solution is adjusted to 20° C., and the initiators, a redox system comprising 2.2 g of 2,2'-azobisamidinopropane dihydrochloride, dissolved in 20 g of water, 6 g of potassium peroxydisulphate, dissolved in 170 g of water, and 0.15 g of ascorbic acid, dissolved in 120 g of water, are subsequently added and the mixture is left to stand without stirring. The gel which forms due to polymerisation is subsequently comminuted mechanically, dried at temperatures above 80° C. and ground.

EXAMPLE 3

2,900 g of demineralised water are introduced under adiabatic conditions into a 5 l cylindrical wide-neck reaction flask, 1,250 g of a commercially available starch which is soluble in cold water, 15 g of the product from N), 1,250 g of acrylic acid and 0.625 g of tetraallyloxyethane are dissolved therein, and the mixture is adjusted to 20° C. Nitrogen (about 2 l/min) is passed into the monomer solution in order to reduce the oxygen content. 34 g of a 4% strength aqueous solution of 2,2'-azobis(amidinopropane) dihydrochloride are added at an $O_2$ content of about 0.8 ppm, 17 g of a 0.75% strength $H_2O_2$ solution are added after further $N_2$ has been passed in and at an $O_2$ content of about 0.08 ppm, and finally 4.5 g of a 0.15% strength ascorbic acid solution are added at an $O_2$ content of about 0.01 ppm. A solid gel forms due to commencing polymerisation, during the course of which the temperature increases to about 90° C., and the gel is subsequently comminuted mechanically. 1,000 g of the comminuted gel are treated with 346 g of 27% strength sodium hydroxide solution (degree of neutralisation of the acrylic acid=70 mol %), the mixture is kneaded thoroughly three times and subsequently dried in a thin layer at temperatures above 100° C., ground and, if desired, screened.

Further examples of the preparation of graft polymers according to the invention as per Examples 1 and 2 described here are summarised in the table below. The amount data denote % by weight, based on the total monomer content. In each case, the compound of the general formula IIa used was maize starch.

The following abbreviations are used:
AA: acrylic acid
MAA: methacrylic acid
CTA: crotonic acid
VPA: vinylphosphonic acid
VPE: vinylphosphonic monoester
AMP: 2-acrylamido-2-methyl-propanesulphonic acid
AMPP: 2-acrylamido-2-methyl-propanephosphonic acid
TMPTA: trimethylolpropane triacetate
TAE: tetraallyloxyethane
MBA: methylenebisacrylamide

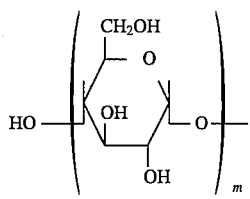

with 49 to 99% by weight of a radical of the formula IIIa

or an alkali metal salt, ammonium salt or amine salt thereof and 0.1 to 2% by weight of a monomer containing at least two olefinically unsaturated double bonds and modifying it by application of carboxyl reactive compounds to its surface, where $X^1$ is $(C_1\text{-}C_{22})$-alkyl, aryl, aralkyl, $COCH_3$, $CH_2COOR^2$, $COCH_2CH_2COOH$, $COOR^2$, $CH_2COCH_2COOR^2$, $CO\text{—}CH=CH\text{—}COOH$,

| Example | Prepared analogously to example | AA (%) | MAA (%) | AMP (%) | AMPP (%) | VPA (%) | VPE (%) | CTA (%) | Graft base Ia as in | IIa (%) | MBA (%) | TMPTA (%) | TAE (%) | Degree of neutralisation (%) |
|---|---|---|---|---|---|---|---|---|---|---|---|---|---|---|
| 4 | 1 | 89.4 | | | | | | | E 5 | 5 | | 0.6 | | 45 |
| 5 | 1 | 89.4 | | | | | | | F 5 | 5 | | 0.6 | | 45 |
| 6 | 1 | 87.4 | | | | | | | G 10 | 2 | | 0.6 | | 45 |
| 7 | 1 | 89.4 | | | | | | | H 5 | 5 | | 0.6 | | 45 |
| 8 | 1 | 89.4 | | | | | | | J 5 | 5 | | 0.6 | | 45 |
| 9 | 1 | 89.4 | | | | | | | K 5 | 5 | | 0.6 | | 45 |
| 10 | 1 | 87.5 | | | | | | | L 10 | 1 | | 1.5 | | 70 |
| 11 | 1 | 87.4 | | | | | | | M 5 | 5 | | 0.6 | | 45 |
| 12 | 2 | 79.7 | | | | | | | C 10 | 10 | 0.3 | | | 75 |
| 13 | 2 | 84.4 | | | | | | | C 10 | 5 | | | 0.6 | 78 |
| 14 | 1 | 78.4 | | | | | | | C 1 | 20 | | 0.6 | | 45 |
| 15 | 1 | 55.0 | 10.0 | 9.5 | | | | | C 10 | 15 | | | 0.5 | 48 |
| 16 | 2 | 63.25 | | 25.0 | | 4.0 | | | C 5 | 2 | 0.25 | | | 45 |
| 17 | 2 | 73.0 | 5.0 | 10.0 | | | 4.2 | | C 5 | 2 | | 0.8 | | 60 |
| 18 | 2 | 83.0 | | 5.0 | 4.5 | | | | C 5 | 2 | 0.5 | | | 70 |
| 19 | 1 | 69.4 | | 20.0 | | 4.2 | | | C 3 | 3 | 0.4 | | | 80 |
| 20 | 1 | 77.0 | 10.0 | | | | 4.0 | | C 4 | 4 | | 1.0 | | 36 |
| 21 | 2 | 85.0 | | | 4.6 | | | | C 5 | 5 | | | 0.4 | 25 |
| 22 | 2 | 78.0 | | 19.0 | | | | | C 1 | 1 | | 1.0 | | 40 |
| 23 | 1 | 69.0 | | 19.3 | | | | 5.0 | C 3 | 3 | | 0.7 | | 48 |
| 24 | 1 | 82.0 | | | | 1.0 | | | C 8 | 8 | | 1.0 | | 32 |

We claim:

1. Mixture of hydrophilic, swellable graft polymers obtained by reacting 0.5 to 50% by weight of a mixture of a polyalkylene oxide compound of the formula Ia

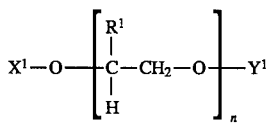

or an alkali metal salt, ammonium salt or amine salt thereof and a compound of the formula IIa

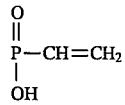

or $SO_3H$ $Y^1$, is $COCH_3$, $CH_2COOR^2$, $COCH_2CH_2COOH$, $CO\text{—}CH=CH\text{—}COOalkyl$, $CO\text{—}CH=CH\text{—}COOH$, $CH_2COCH_2COOR^2$, $COOR^2$, $SO_3H$ or

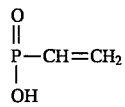

n and m, independently of one another, are 2 to 300, $R^1$ is hydrogen or methyl, $R^2$, independently of one another, are hydrogen, methyl or ethyl, $R^3$ is the carboxyl group, the sulphonyl group, the phosphonyl group, which is optionally esterified by means of alkanol having 1 to 4 carbon atoms, or a group of the formula

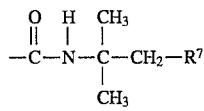

in which $R^7$ is the sulphonyl group or the phosphonyl group, and $R^4$ is hydrogen, methyl, ethyl or the carboxyl group, are reacted under the conditions of gel polymerization.

2. Mixture of graft polymers according to claim 1, wherein the carboxyl-reactive compounds are selected from the group consisting of glycidyl ethers of polyhydric alcohols, glycidyl phosphonates, polyamines, polyamidoamines, 3-aminopropyltriethoxysilane, trimethoxysilylproyldiethylene triamine, N-aminoethylaminopropyltrimethoxysilane, aminoethylaminomethylphenethyltrimethoxysilane and 3-glycidyloxypropyltrimethoxysilane.

3. Mixture of graft polymers according to claim 2, wherein the glycidyl ethers of polyhydric alcohols are monoethylene glycol diglycidylether or polyethylene glycol diglycidyl ether.

4. Mixture of graft polymers according to claim 2, wherein the glycidyl ethers of polyhydric alcohols are nonaethylene glycol diglycidyl ether, monopropylene glycol diglycidyl ether or polypropylene glycol diglydicyl ether.

5. Graft copolymers according to claim 1, wherein in a random distribution, from 0.5 to 20% by weight of radicals of the general formulae Ia and IIa, from 79 to 99% by weight of radicals of the general formula IIIa and from 0.1 to 1.8% by weight of crosslinking structures.

6. Graft polymers according to claim 5, wherein in a random distribution, from 1 to 15.5% by weight of radicals of the general formulae Ia and IIa, from 83 to 98.5% by weight of radicals of the general formulae IIIa and from 0.3 to 1.5% by weight of crosslinking structures.

7. Graft polymers according to claim 6, wherein in the radicals of the formula Ia differ from one another with respect to the radical $R^1$ and/or the number n.

8. Graft polymers according to claim 7, wherein $R^2$ is hydrogen or methyl, $R^3$ is the carboxyl group, the sulphonyl group or the phosphonyl group, and $R^4$ is hydrogen.

9. Graft polymers according to claim 8, wherein the crosslinking structures are derived from monomers containing at least two alkyl groups or at least two alkenyl groups.

10. Hydrophilic, swellable graft polymers, which comprises radicals of the formula

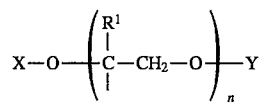

and radicals of the formula III

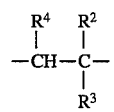

and
a radical of the formula II

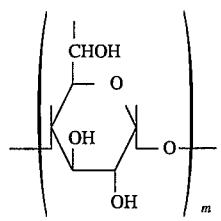

and radicals of a crosslinking agent which are derived from monomers containing at least two olefinically unsaturated double bonds, where X and Y, independently of one another, are $COCH_3$, $CH_2COOR^2$, $COCH_2CH_2COOH$

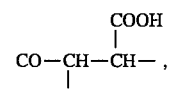

$COOR^2$, $CH_2COCH_2COOR^2$, $SO_3H$ or

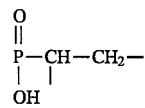

n and m, independently of one another, are 2 to 300, $R^1$ is hydrogen or methyl, $R^2$, independently of one another are hydrogen, methyl or ethyl, $R^3$ is the carboxyl group, the sulphonyl group, the phosphonyl group, which is optionally esterified by means of alkanol having 1 to 4 carbon atoms, or a group of the formula

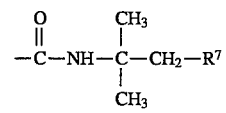

in which $R^7$ is the sulphonyl group or the phosphonyl group, and $R^4$ is hydrogen, methyl, ethyl or carboxyl group, wherein the total of radicals of the formulae I and II are 0.5 to 50% by weight, the total of radicals of the formula III is 49 to 99% by weight and the total of radicals of a crosslinking agent is 0.1 to 2% by weight, said mixture of graft polymers being modified by application of carboxyl-reactive compounds to its surface.

11. Mixture of graft polymers according to claim 10, wherein the carboxyl-reactive compounds are selected from the group consisting of glycidyl ethers of polyhydric alcohols, glycidyl phosphonates, polyamines, polyamidoamides, 3-aminopropyltriethoxysilane, trimethoxysilylpropyldiethylene triamine, N-aminoethylaminopropyltrimethoxysilane, aminoethylaminomethylphenethyltrimethoxysilane and 3-glycidyloxypropyltrimethoxysilane.

12. Mixture of graft polymers according to claim 11, wherein the glycidyl ethers of polyhydric alcohols are monoethylene glycol diglycidylether or polyethylene glycol diglycidyl ether.

13. Mixture of graft polymers according to claim 11, wherein the glycidyl ethers of polyhydric alcohols are nonaethylene glycol diglycidyl other, monopropylene glycol diglycidyl ether or polypropylene glycol diglydicyl ether.

* * * * *